United States Patent [19]

Gimbel

[11] Patent Number: 4,485,498
[45] Date of Patent: Dec. 4, 1984

[54] INTRAOCULAR LENS SYSTEM

[76] Inventor: Howard V. Gimbel, 103 - 1711 - 4 St. SW., Calgary, Alberta, Canada, T2S 1V7

[21] Appl. No.: 404,290

[22] Filed: Aug. 5, 1982

Related U.S. Application Data

[62] Division of Ser. No. 156,072, Jun. 3, 1980, Pat. No. 4,342,123.

[51] Int. Cl.³ .......................... A61F 1/16; A61F 1/24
[52] U.S. Cl. ........................................................ 3/13
[58] Field of Search ........................................... 3/13, 1

[56] References Cited

U.S. PATENT DOCUMENTS

| | | | |
|---|---|---|---|
| 3,925,825 | 12/1975 | Richards et al. | 3/13 |
| 3,994,027 | 11/1976 | Jensen et al. | 3/13 |
| 3,996,626 | 12/1976 | Richards et al. | 3/13 |
| 4,012,823 | 3/1977 | Richards | 3/13 X |
| 4,073,015 | 2/1978 | Peyman et al. | 3/13 |
| 4,085,467 | 4/1978 | Rainin et al. | 3/13 |
| 4,092,743 | 6/1978 | Kelman | 3/13 |
| 4,104,339 | 8/1978 | Fetz et al. | 3/13 X |
| 4,124,905 | 11/1978 | Clark | 3/13 |
| 4,177,526 | 12/1979 | Kuppinger | 3/13 |
| 4,242,760 | 1/1981 | Rainin | 3/13 |

Primary Examiner—Ronald L. Frinks
Attorney, Agent, or Firm—William R. Hinds

[57] ABSTRACT

Attachment means for an artificial intraocular lens system for implantation in the eye comprises a pair of capsule clips laterally extending from the edge of the lens and lying within or parallel to the plane of the lens, and at least a single clip diametrically opposed to the pair of clips. The members of the pair of capsule clips are resiliently biased into co-planar alignment or biased against separation. The members of the pair of capsule clips may have serrations for more secure engagement of the capsule.

10 Claims, 14 Drawing Figures

INTRAOCULAR LENS SYSTEM

This is a division of application Ser. No. 156,072 filed June 3, 1980, now U.S. Pat. No. 4,342,123.

BACKGROUND OF THE INVENTION

This invention relates to attachment means for an artificial intraocular lens intended for implanting within the human eye, for the correction of aphakia.

The use of artificial intraocular lenses for the correction of aphakia is well established and a variety of such lenses with diverse means for securing the lens in position adjacent the iris are disclosed in the patent literature. Such attachment means, usually diametrically disposed on the periphery of the circular lens, are adapted to be engaged by the iris on its anterior and posterior surfaces, and in some cases adapted to be sutured in position for stabilization within the eye. Other attachment means require a loop to be placed within the capsular bag and held in position by the iris until fibrosis secures it to the capsule. However, such prior art fixation means are uncertain and have required immobilization of the iris for extended periods to permit the development of anchoring ocular tissue; inadvertent movement of the implant normally requires additional remedial eye surgery.

It is an object of the present invention to overcome the problems of the prior art devices which rely on ocular tissue fibrosis into the attachment means, for stabilization within the eye, and an attachment means is now described for implant procedures, which is positive in its action without requiring the iris to hold the lens in position while fibrosis occurs.

As will be appreciated, the normal lens of an eye is a clear protein gelatinous material, not unlike the white of an egg, encased in a capsule, or as is commonly called, a capsular bag.

SUMMARY OF THE INVENTION

In accordance with the present invention, there is provided attachment means for an artificial intraocular lens adapted to readily hold the lens in place on the capsule. The lens is made of polymethylacrylate or other biologically tolerable optically suited material, and is formed in conventional circular, convex configuration, having a principal plane, known as the "plane of the lens" and an optical axis perpendicular thereto. A pair of inter-acting capsule clips, lying generally in the plane of the lens or parallel with the plane of the lens at least one member of which is lightly biased into a normal co-planar or close alignment of the pair, is secured to the lens at a point on its periphery in the manner hereinafter described. Fixedly secured to the lens at a point on its periphery in diametrical opposition to the inter-acting pair of clips, is at least one single clip of generally similar configuration. While in the preferred embodiment, the clips are formed of monofilament plastic of the same composition as the lens itself, metal wire or other biologically tolerable materials may be used. In an alternative construction hereinafter described, the clips are of solid construction as distinct from the loop construction first described, and take the configuration of laterally extending tab members, a paired and a single, in diametrically opposed disposition, mounted on the lens. It has been found that the combination of the pair of peripherally mounted inter-acting clips, and the diametrically opposed single clip, provides fixation means which assure ease of insertion with improved post-insertion stability of the intraocular lens.

Following preparation of the aphakic eye, which, for purpose of explanation includes the surgical removal of a portion of the anterior surface of the capsular bag, and extraction of the protein material, the opening, or window, thus provided in the capsular bag provides first and second diametrically opposed flap portions adapted to facilitate attachment of the lens system in accordance with the present invention.

In use, subsequent to surgery, the two co-acting members of the pair of capsule clips are deployed for insertion by spreading them apart, as with a length of suture material of suitable diameter, so that they assume a slightly non-planar or more separated aspect. The lens is then inserted into position in the eye, anterior to the iris, or posterior to the iris, with the single clip engaging the posterior surface of a first flap of the capsular bag at a point, the pair of deployed co-acting capsule clips being attached to the second, diametrically opposed flap. Withdrawal of the suture material from between the two members of co-acting capsule clips allows them to reassume their coplanar or less separated positions. Thusly, the requirement of further suturing into position, or the likelihood of subsequent risk of dislocation of the artificial lens within the now closed eye chamber, are avoided.

BRIEF DESCRIPTION OF THE DRAWINGS

The invention will now be described in greater detail with reference to the accompanying drawings which illustrate preferred embodiments of the invention, and wherein.

DESCRIPTION OF THE PREFERRED EMBODIMENTS(S)

Figure 1:
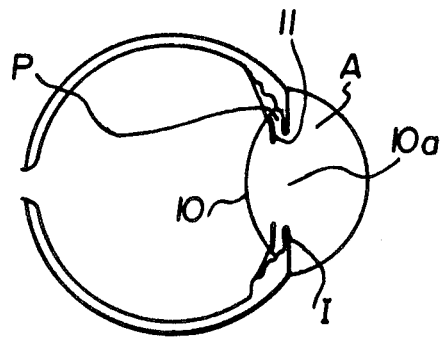
FIG. 1 is a sectional view through a human eye, the aphakic eye prepared for deployment of the lens system according to the present invention (with crystalline lens nucleus removed, leaving the posterior wall of the capsule bag intact, and with a portion of the anterior wall of the capsule bag removed)
Figure 4:
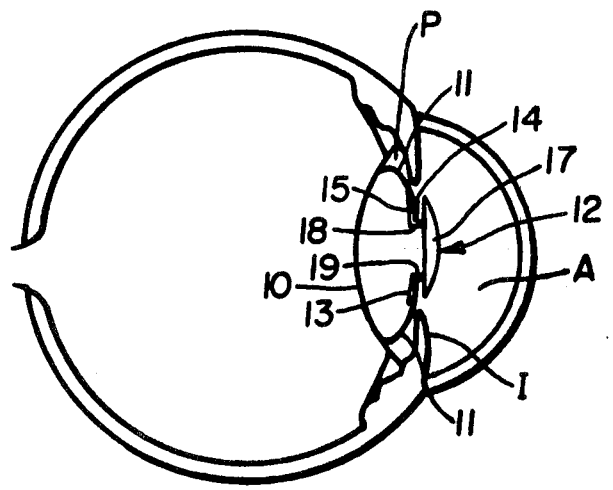
FIG. 4 is a sectional view through the human eye, with the lens system of FIGS. 2 and 3 in place.

Referring firstly to FIG. 1, a sectional view of an eye is depicted, as prepared by surgery, for implantation of the lens system of the invention. The anterior chamber A, and the posterior chamber P, of the eye are separated by the iris I, which lies immediately anterial of the natural crystalline lens of the normal (aphakic) eye. As mentioned heretofore, the natural lens is contained within a capsule, or capsular bag, and in FIG. 1, the crystalline material has been removed from the capsule 10, and an opening or window 10a, provided in the anterior wall of the bag 10, adjacent the pupillary opening in the iris I. The capsular tissue or flaps 11, surrounding window 10a, provides for the attachment of the lens system as will be hereinafter more specifically described. Following removal of the crystalline lens, consequent on cataract surgery, an artificial lens 12 is mounted in the location previously occupied by the crystalline lens, and is normally mounted anterior of the iris I, as indicated in FIG. 4, with the plane of the lens substantially parallel to the plane of the iris I. The pupillary opening in the iris I is expanded to permit the single clip 13 to be inserted within the capsular bag beneath one side flap 11, and after spreading apart the two members 14 and 15 of the pair of capsule clips, as with a length of suture material, the pair of clips are positioned to engage diametrically opposed capsular flaps 11, as indicated in FIG. 4, whereupon the spreading suture is withdrawn, permitting the clip members 14 and 15 to firmly engage the capsular flap as indicated in FIG. 4. Thus held in its optically proper position, the lens system 12 is secure while tissue growth develops around the clips 13, 14 and 15, to even more securely anchor the lens system in place.

Figure 2:
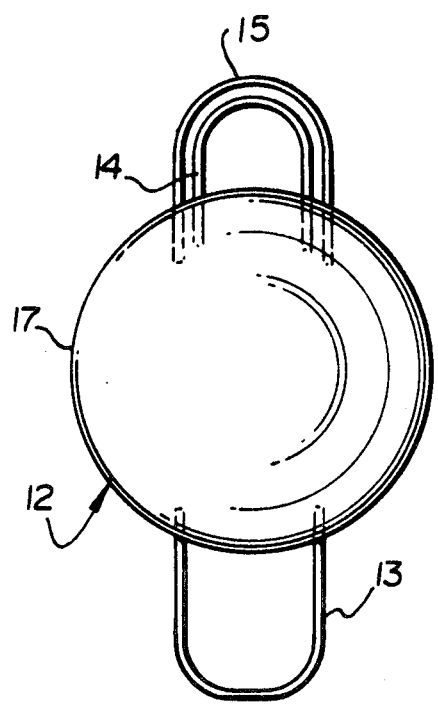
FIG. 2 is a plan view of the improved lens and lens attachment means, in the preferred embodiment of the present invention.
Figure 3:
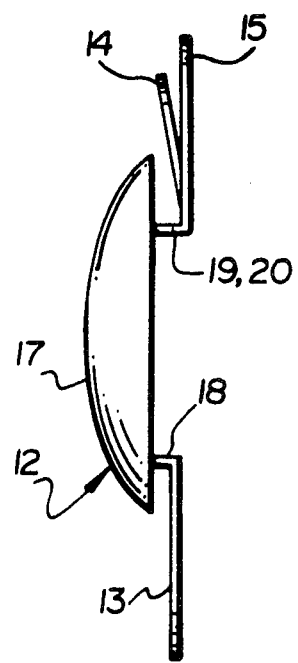
FIG. 3 is a side view of the preferred embodiment according to FIG. 2.

In the preferred embodiment, depicted in FIGS. 2 and 3, the lens system 12 comprises a lens body 17, and attachment portions comprising the single clip 13 and the co-acting pair of clips consisting of clip members 14 and 15. The clip members 13, 14 and 15, are formed of monofilament rsilient material, the lens body 17 being drilled for blind holes to receive the leg portions 18, 19 and 20, respectively of the clip members 13, 14 and 15. Bonding of the clips in a manner known per se, follows insertion into the drillings in the lens body 17.

As will be appreciated, a posterior lens system (FIG. 6) may be utilized in which the capsular attachment means are positioned on the lens body in the plane of the lens. The mounting procedure is substantially the same as with the prepupular embodiment depicted in FIG. 4, just described.

Figure 5:
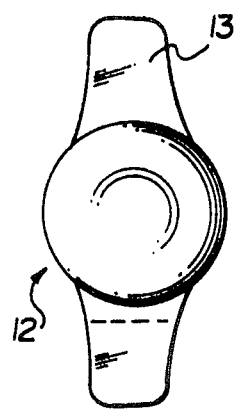
FIGS. 5 and 5(a) are respectively, plan and side views of a second embodiment of the present invention, in which the clip members are of solid construction.
Figure 5A:
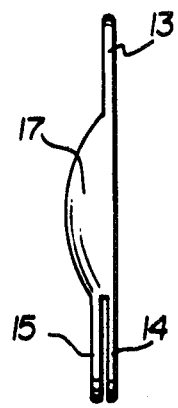

Referring now to FIGS. 5 and 5(a), there is illustrated a modified construction of the lens system 12, in which the lens body 17, a single solid tab 13 and a pair of diametrically oppositely disposed double tabs 14 and 15 are all integrally molded in a unitary construction, of dimensions generally similar to the lens system 12 of FIG. 2, into radially projecting tabs mounted on the periphery of the lens body 17. Mounting procedures will be similar to the procedures described for the lens system 12, and the holding action of the pair of tabs 14 and 15 will be seen to be a simple squeeze action on the capsular bag tissue, which can be regulated in accordance with the selection of materials and physical dimensions of the tab members 14 and 15.

Figure 6:
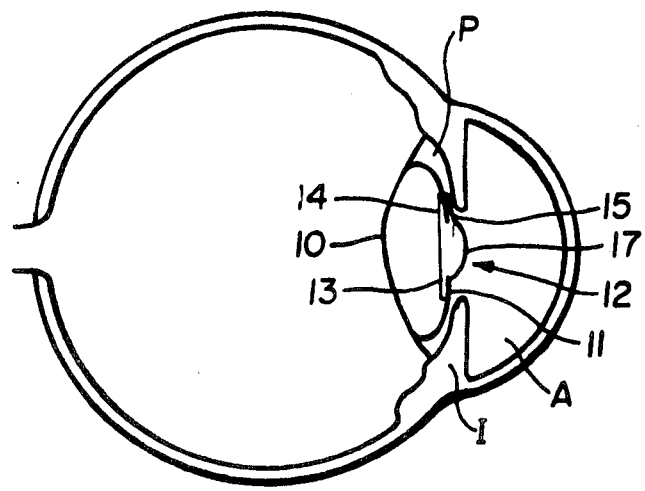
FIG. 6 is a sectional view through the human eye, with the lens system of FIGS. 5 and 5(a) in place.

FIG. 6 shows a sectional view of the eye with the lens system, as described above, with reference to FIGS. 5 and 5(a).

Figure 7:
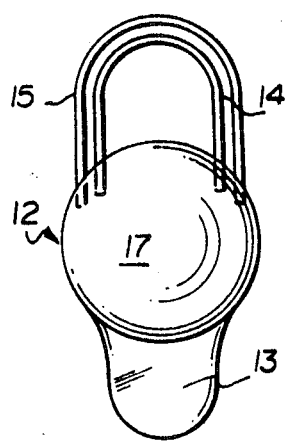
FIGS. 7 and 7(a) are plan views of further embodiments of the present invention, combining certain features of the preferred embodiments of FIG. 2 and FIG. 5.
Figure 7A:
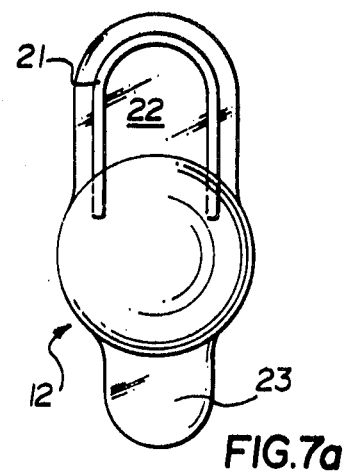

FIG. 7 is a still further modification of the lens systems depicted in FIGS. 2, 3, and 5, in which the fixation means comprise a combination of the pair of lens co-acting clips 14 and 15 of FIG. 2, and the diametrically oppositely disposed solid tab 13 of FIG. 5. It will be understood, of course, that the combinations may also be reversed, with the co-acting pair of tabs 14 and 15 of FIG. 5 combined with the single clip 13 of FIG. 1. Or, alternatively, as depicted in FIG. 7(a), a single loop member 21 is biased against a co-acting solid tab 22, in opposition with a single solid tab 23.

Figure 8:
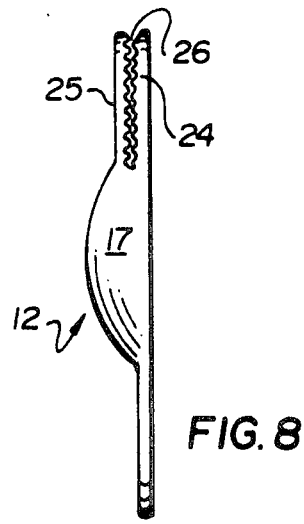
FIGS. 8 and 8(a) depict, respectively, a side view and fragmentary plan view of a still further variant of the lens system of FIG. 5.
Figure 8A:
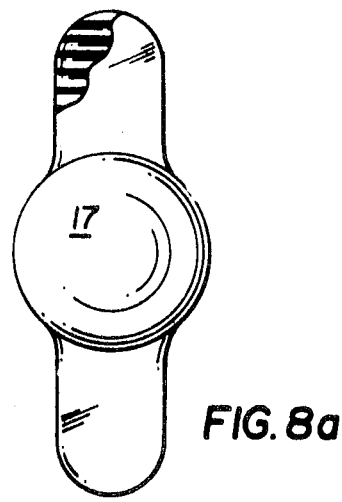

A still further modification of the lens system 12 of FIG. 1 is depicted in FIGS. 8 and 8(a) in which the clip members 24 and 25 of the pair of capsule clips are provided with a plurality of serrations 26, adapted to engage more firmly the flaps of the capsular bag. The serrations 26 may be formed by grooving the anterior and posterior surfaces of the pair of clip members 24 and 25 as depicted. It will be understood that in use, the serrations 26 are modifications of the basic embodiment of FIG. 1, adapted to more securely engage the capsular bag prior to the establishment of ocular tissue growth permanently anchoring the lens system in position.

It will be appreciated that the functioning of the present invention, as heretofore described, depends on the interaction of the two members of the paired clip members for secure engagement of the capsular bag, the pair of clip members cooperating with a single diametrically opposed single clip member to thus stabilize the implant. None of the lens attachment systems described in the prior art appear to have successfully engaged this problem.

Figure 9:
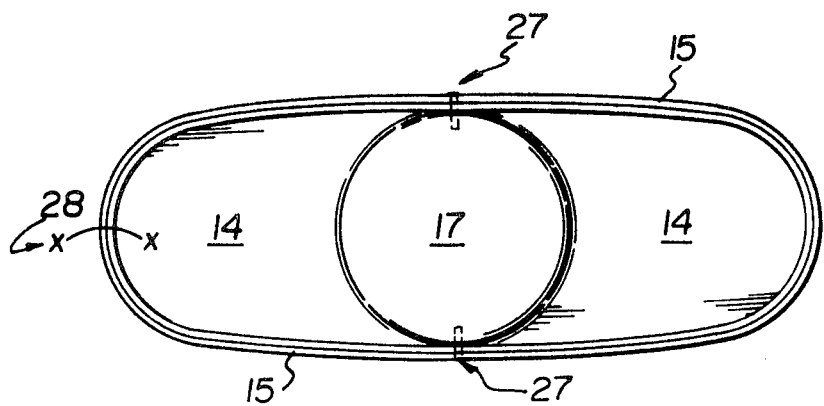
FIGS. 9, 9(a) and 9(b) respectively, show in plan and side elevation, a further embodiment of the present invention utilizing a "hinged" clip member.
Figure 9A:
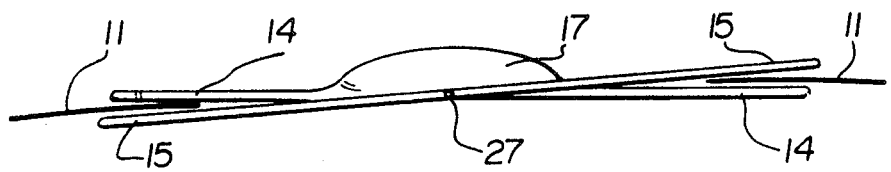
Figure 9B:
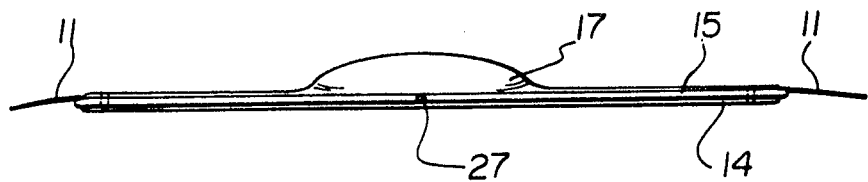

Finally, referring to FIGS. 9, 9(a) and 9(b), there is shown a further alternative lens construction according to the present invention which utilizes a "hinged" clip arrangement.

FIG. 9 shows in plan view the lens body 17, which in this embodiment is provided with a pair of diametrically oppositely disposed single tabs 14, integrally molded with the lens body 17 in a unitary construction, and a generally oval single clip 15, which circumferentially extends about body 17 and tabs 14.

Clip 15 is pivotally attached to lens body 17 at diametrically opposed pivot points 27.

The principle of surgically clipping the implant, whether a prepupillary or posterior implant, should be readily appreciated from FIGS. 9(a) and 9(b). With reference to FIG. 9(a), clip 15 has been pivotally opened such that the capsular flaps 11 can be inserted between tabs 14 and 15. By rotating clip 15 about pivot points 27 into general realignment with the body of the lens as shown in FIG. 9(b), the capsular flaps 11 are firmly held between clip 15 and tabs 14 and can be maintained so, for example, as shown schematically, in FIG. 9 by a suture 28.

It has been found, therefore, that the simple, easily constructed and convenient intraocular lens of the present invention, as described herein, provides an effective, secure and permanent mounting means with a minimum of trauma to the eye.

The embodiments shown and described are by way of example and it is to be understood that many changes and modifications might be made thereto without departing from the spirit of the invention. For example, while in the embodiments heretofor described with reference to FIGS. 1-8, the lens attachment means includes a pair of diametrically opposed haptics, one of the pair comprising one clip member and the other of the pair comprising two cooperating clip members, it will be appreciated that the attachment means could include two cooperating pairs of clip members, diametrically opposed one with the other. The invention is, therefore, not to be construed as limited to the embodiments shown and described, except insofar as the claims may be so limited.

What I claim is:

1. An artificial intraocular lens system constructed and arranged to be implanted within an opening in the capsular bag of the normal lens of an eye immediately adjacent the iris of the eye to supplant or replace the normal lens of the eye, comprising an optical lens portion formed of biologically tolerable, optically suited material so as to have an optical axis, and attachment means extending generally radially outwardly from said lens portion at spaced positions about its periphery for engaging parts of the capsular bag surrounding said opening so as to secure said lens portion in the opening, said attachment means including, at at least one position about said periphery, two cooperating members which extend generally radially outwardly and are axially separatable for receiving and securing therebetween a part of the capsular bag surrounding said opening, such that the respective members bear against inner and outer surface portions of said capsular bag to assist in securing said lens portion in position in said opening, the cooperating surface portions of said members being so closely spaced in the normal condition of said members as to require separation of the members to receive a part of the capsular bag surrounding said opening, and so as to secure between them a part of the capsular bag when the members move back toward their normal condition, such that the members assist in securing said lens portion independently of the iris.

2. An artificial intraocular lens as claimed in claim 1 wherein at least one of said members is of resilient material.

3. An artificial intraocular lens system as claimed in claim 1 wherein said cooperating surface portions of said members are normally slightly spaced by a distance not greater than the thickness of the capsular bag wall.

4. An artificial intraocular lens as claimed in claim 3 wherein said spacing is less than the thickness of the capsular bag wall.

5. An artificial intraocular lens system as claimed in claim 1 wherein said members are normally coplanar.

6. An artificial intraocular lens system as claimed in claim 1 wherein one of said members is pivotally attached so as to be pivotally movable toward and away from the other member.

7. An artificial intraocular lens as claimed in claim 6 wherein one of said members normally lies within the other member so as to be at least partially surrounded thereby.

8. An artificial intraocular lens as claimed in claim 1 wherein said members are normally slightly axially spaced by a distance not greater than the thickness of the capsular bag wall.

9. An artificial intraocular lens as claimed in claim 8 wherein said axial spacing is less than the thickness of the capsular bag wall.

10. An artificial intraocular lens as claimed in claim 1 wherein said members are resiliently biased against separation of their cooperating surface portions.

* * * * *